(12) United States Patent
Clavey

(10) Patent No.: US 9,309,178 B2
(45) Date of Patent: Apr. 12, 2016

(54) PROCESS FOR PREPARING ACETALS AND KETALS

(75) Inventor: Thomas Clavey, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/130,682

(22) PCT Filed: Jun. 29, 2012

(86) PCT No.: PCT/EP2012/062742
§ 371 (c)(1),
(2), (4) Date: Apr. 3, 2014

(87) PCT Pub. No.: WO2013/004626
PCT Pub. Date: Jan. 10, 2013

(65) Prior Publication Data
US 2014/0323771 A1    Oct. 30, 2014

(30) Foreign Application Priority Data

Jul. 6, 2011    (EP) .................................... 11172866

(51) Int. Cl.
  *C07C 41/56*   (2006.01)
  *C07C 41/58*   (2006.01)
  *B01D 61/36*   (2006.01)

(52) U.S. Cl.
  CPC .............. *C07C 41/56* (2013.01); *B01D 61/362* (2013.01); *C07C 41/58* (2013.01); *B01D 2311/04* (2013.01); *B01D 2311/263* (2013.01); *B01D 2317/022* (2013.01)

(58) Field of Classification Search
  None
  See application file for complete search history.

(56) References Cited

U.S. PATENT DOCUMENTS

| 5,892,129 | A | * | 4/1999 | Hoepp et al. | 568/600 |
| 6,806,392 | B2 | * | 10/2004 | Boesch et al. | 568/594 |
| 2004/0024260 | A1 | * | 2/2004 | Winkler et al. | 568/591 |
| 2014/0288333 | A1 | * | 9/2014 | Clavey | 568/594 |

FOREIGN PATENT DOCUMENTS

EP    1 167 333    1/2002

OTHER PUBLICATIONS

International Search Report for PCT/EP2012/062742, mailed Oct. 2, 2012.

* cited by examiner

*Primary Examiner* — Brian J Davis
(74) *Attorney, Agent, or Firm* — Nixon & Vanderhye P.C.

(57) ABSTRACT

The present invention is concerned with a process for preparing acetals and ketals which comprises (i) reacting an aldehyde or ketone with an alcohol in the presence of a solid acid at a temperature of below −40° C., and (ii) removing water and lower aliphatic alcohol and/or sugar alcohol from the reaction product by pervaporation.

14 Claims, 1 Drawing Sheet

PROCESS FOR PREPARING ACETALS AND KETALS

This application is the U.S. national phase of International Application No. PCT/EP2012/062742 filed 29 Jun. 2012 which designated the U.S. and claims priority to EP Patent Application No. 11172866.3 filed 6 Jul. 2011, the entire contents of each of which are hereby incorporated by reference.

The present invention is concerned with a novel process for preparing acetals and ketals.

As it is known, acetals and ketals can be prepared by reacting an aldehyde or ketone with an alcohol in the presence of an acidic catalyst. However, the reaction is reversible and, at ambient temperature or above, the equilibrium of the reaction is shifted to the side of the starting materials, acetal or ketone, and alcohol.

The processes known form the prior art (for example EP1167333), which are used in plants today, require several rectification (purification) steps. Such a process can be time-consuming and produces a high amount of $CO_2$-emissions. Therefore, the goal of the present invention was to find a process, which allows the production of acetals and ketals which is a simplified reaction process, and which does not have the disadvantages as listed above.

Thus, the invention is concerned with a process for the preparation of acetals or ketals that comprises reacting an aldehyde or ketone with an alcohol in the presence of a solid acid at temperatures below −40° C. and removing water and lower aliphatic alcohol and/or sugar alcohol from the reaction product by pervaporation.

As a further advantage, this process according to the present invention allows a simplified working up of the unreacted starting material.

Figure 2:
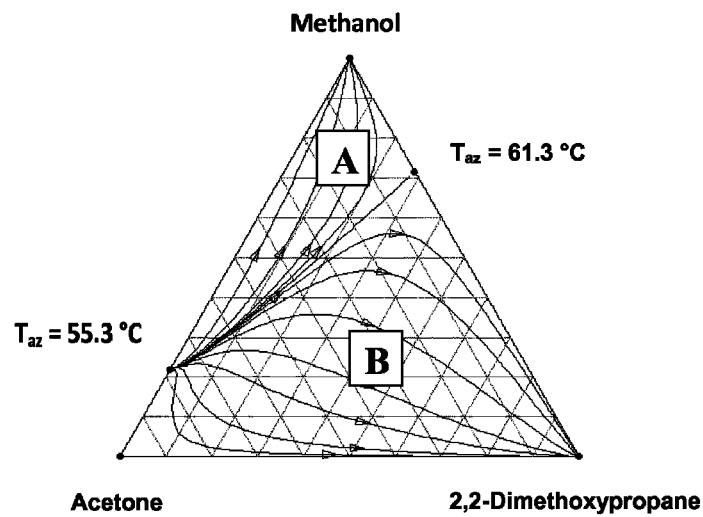

The process according to the present invention allows traversing the azeotropic limiting line of the reaction mixture (FIG. 2.). Therefore, the recovery of the unreacted starting materials of the reaction can be carried out in one single rectification unit. This process reduces the time consumption and the $CO_2$-emissions when compared to the processes known form the prior art.

The removal of traces of the reaction water obtained at the bottom product of the above mentioned rectification unit can be carried out in another pervaporation unit. The in this way purified acetals and/or ketals can be processed further.

More specifically, the present invention is concerned with a process for removing water and lower aliphatic alcohol and/or sugar alcohol from reaction mixtures obtained by reacting an aldehyde or ketone with an alcohol, particularly by reaction of a lower aliphatic aldehyde or ketone with a lower aliphatic alcohol or sugar alcohol, in the presence of an acid at a temperature of below −40° C. which process comprises subjecting the reaction mixture containing an acetal or ketal together with water and unreacted aldehyde or ketone and alcohol, to treatment with a base, by pervaporation.

The term "lower" as used herein denotes compounds having 1 to 7 carbon atoms. Examples of lower aliphatic ketones are acetone and methyl ethyl ketone. Examples of lower aliphatic aldehydes are formaldehyde, acetaldehyde, propionic aldehyde, butyric aldehyde and isobutyric aldehyde. Examples for lower alcohols are methanol and ethanol. Sorbose is an example of a sugar alcohol.

Pervaporation is a known method for separating liquids from mixtures thereof, e.g., for separating water from mixtures with organic liquids, such as alcohols, aldehydes or ketones, see, e.g., European Patent No. 0 096 339, and Chem. Eng. Technol. 19 (1996) 117-126. In pervaporation processes, the different ability of liquids or gases to permeate polymer membranes is used to separate mixtures thereof.

Pervaporation has been proposed to separate water e.g., from esterification reactions. Also, the successful application of the removal of reaction water from acetalisation or ketalisation processes has been reported (U.S. Pat. No. 6,806,392). The focal point of these processes is the removal of water in order to shift the equilibrium to the side of the product side. This process of the prior art do not lead to traverse the azeotropic limiting line of the reaction mixture (FIG. 2.). The process of this invention can be applied to any acetalisation and ketalisation reaction.

Examples of such reactions are

Conversion of acetone to 2,2-dimethoxypropane;
Conversion of methyl ethyl ketone to dimethoxybutane;
Conversion of sorbose to sorbose diacetonide;
Conversion of butendiol to isopropoxydioxepen;
Conversion of methyl glyoxal to dimal.

In a more preferred aspect, the process of this invention is used to prepare 2,2-dimethoxypropane from acetone and methanol. In the first step of the reaction in accordance with the invention the solid acid is suitably a strongly acidic polymer such as a polystyrene sulfonic acid, which may be macroporous or gel-type. Ion exchange resins conventionally used to catalyze ketalisation reactions can be used. Examples of such ion exchange resins are Dowex 50 (Dow Chemical), Amberlite IR 120, Amberlyst A 15 and A 36 (Rohm & Haas), Lewatit (Bayer).

The reaction temperature for a process according to the present invention is below −40° C. The reaction temperature is suitably from about −100° C. to about −40° C., preferably from about −80° C. to about −45° C. Examples of bases as used in the second reaction step are weakly basic ion exchange resins such as polystyrenes resins carrying quaternary ammonium groups, e.g. IRA 96 (Rohm & Haas).

For the pervaporation, any membrane which is resistant to the reaction products and which are permeable for water may be used. Examples of such membranes are hydrophilic membranes which may be polymer or inorganic ceramic membranes. Polymer membranes may be composite membranes comprising a support layer, e.g. on the basis of acrylnitril polymers, and a polyvinyl alcohol layer which provides the actual active separating layer. This membrane usually has a flux density for methanol of 2.2 to 5 $kg/(hm^2)$, preferably from 2.2 to 4.9 $kg/(hm^2)$.

Examples of membranes useful in the process of this invention are membranes provided by Sulzer Chemtech Allschwil, Switzerland under the name Pervap 1211, Pervap 2201, Pervap 2255-70 and Pervap 2255-80; as well as membranes provided by CM-CELFA Membrantechnik A G, CH-6423 Seewen, Switzerland, under the name CMC-CE-01, CM-CE-01 and CMC-VP-31. Examples of inorganic membranes useful in the process of this invention are turbular Zeolith A membranes provided by Mitsui Engineering & Shipbuilding Co., Ltd., 3-16, Nihonbashi 1-chome, Chuo-ku, Tokyo 103-0027, Japan, under the name of NaA. Other membranes which are suitable are the Zeolith X, Y and ZSM-5 membranes. Another example of a ceramic membrane is the Hybsi membrane by ECN licensed by Pervatech B V, 7468MC Enter, The Netherlands. The flux density for a ceramic membrane, such as the Hybsi membrane, is usually in the range of 2 to 100 $kg/(hm^2)$, preferably from 3.0 to 73.9 $kg/(hm^2)$.

The pervaporation is suitably carried out at elevated temperatures, i.e., temperatures up to the boiling point of the reaction mixture on the retentate side of the membrane. In general, the pervaporation is carried out at about 60° C. to about 150° C. The pressure in the pervaporation is not critical and is basically determined by the pressure required to sustain the mass flow. However elevated pressure, e.g., up to 10 bar on the retentate side of the membrane can be used, subject to the mechanical resistance of the membrane, to increase the boiling point of the reaction mixture, thus allowing the pervaporation to proceed at higher temperature. The pressure on the permeate side of the membrane is suitably about 1 to about 500 mbar.

Figure 1:
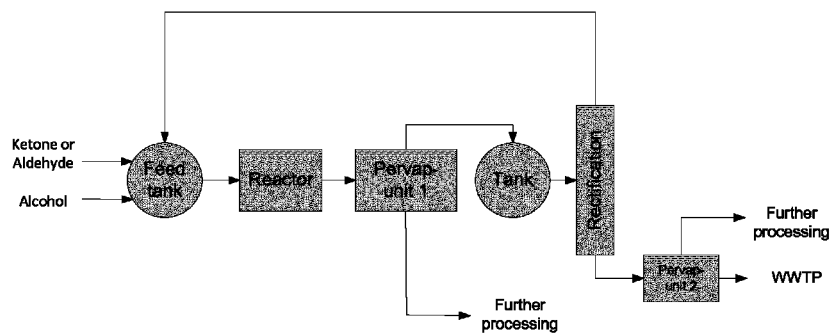

The invention is further illustrated by FIG. 1 which provides a block flow diagramme for obtaining substantially pure 2,2-dimethoxypropane from acetone and methanol, but which may find use for other ketals or aldehydes according to the invention.

According to the process in FIG. 1, a mixture of acetone and methanol in a molar ratio of about 2 to about 6 moles, preferably about 4 moles of methanol to one mole of acetone is cooled and fed into the reactor which contains an acid ion exchange resin. The reactor is cooled to an appropriate temperature favouring ketal formation, e.g., to a temperature of from about −100° C. to about −40° C. The flow of the reaction mixture is controlled to allow the reaction mixture to achieve the state of the equilibrium. Depending on the dimension of the reactor, the mean residence time of the reaction mixture may vary between 1 and 10 minutes. The reaction product exiting the reactor and containing the desired product, 2,2-dimethoxy propane, in admixture with water, acetone and methanol is then fed via a basic ion exchange resin into the pervaporation unit 1. Suitably, a heat exchanger network and a heater is provided between the reactor and the pervaporation unit 1 (not shown in FIG. 1) to allow heat transfer from the acetone/methanol mixture to reaction product exiting the reactor and to adjust the temperature required for the pervaporation (about 60° C. to 150° C.). The permeate from the pervaporation unit 1 consists of methanol, water, minor amounts of acetone and traces of ketal. The retentate from the pervaporation unit 1 contains ketal, acetone, methanol and water that was not fully removed in pervaporation unit 1.

The composition of the retentate leaving the pervaporation unit 1 and entering the rectification unit via a basic ion exchange resin and a storage tank resides after removing most of the methanol in the pervaporation unit 1 in section B shown in FIG. 2. The rectification is carried out at pressures at the top of the column in the range of 100 to 2000 mbar preferable at 1000 mbar. The reflux ration amounts in the range of 0.5 to 4 preferable 1 to 1.75. The top product stream of the rectification unit contains all acetone, methanol, and traces of the ketal. The bottom stream of the rectification unit contains the ketal and water. In the pervaporation unit 2 the remaining water is separated from the ketal. The purified ketal can then sent to further processing.

As will be apparent from the above, the acetalisation and ketalisation reaction is carried out at very low temperature whereas the pervaporation is carried out at elevated temperature. Therefore, in a further aspect of the invention, the heat obtained in cooling the reactants in the acetalisation and ketalisation reaction is used to heat up the equilibrium mixture containing the ketal prior to pervaporation.

FIGURES

FIG. 1: Block flow diagram of the inventive process
FIG. 2: Reaction diagram
The following Example further illustrates the process of this invention.

EXAMPLE

A mixture consisting of 70 wt.-%, based on the total weight of the mixture at the feed, of methanol (factory regenerate; corresponding to ca. 63 wt.-% of pure methanol in total) and 30 wt.-% of acetone was fed into the reactor of an equipment corresponding to the one shown in FIG. 1 with a flow rate of 1.0 kg per hour. The reactors with acid ion exchange resin had a volume of a volume of ca. 0.7 l and were charged with 530 g of AMBERLYST A 15. The vessels with basic exchange resin had a volume of 0.17 l and were charged with 120 g of AMBERLITE IRA 96. The reactors and the connecting tubes were made of glass except the pervaporation unit and the tubes leading from the temperature in the reactors charged with acid ion exchange resin was adjusted to maintain an exit temperature of −64° C. to −66° C. In the pervaporation units the membrane surface was 0.038 m$^2$; the temperature was adjusted to 95° C.; the pressure at the side of the retentate (i.e., before the membrane) was 4 bar (abs.), the pressure at the side of the permeate (i.e., behind the membrane) was 10 to 30 mbar. Membranes of the type Pervap 2255-80 (Sulzer Chemtech) were used. The results obtained are given in the Table below:

|  | Outlet reactor | Retentate Unit 1 | Permeate Unit 1 | Retentate Unit 2 |
|---|---|---|---|---|
| water content | 5.2% | 0.5% | 27.17% | <0.1% |
| ketal content | 30.75% | 37.2% | 0.8% | 99.9% |
| retentate/feed ratio | — | 82.14% | — | 99.36% |

The invention claimed is:

1. A process for the preparation of acetals or ketals which comprises:
   (i) reacting an aldehyde or ketone with an alcohol in the presence of a solid acid at a temperature of below −40° C. to form a reaction product mixture comprising water and a lower aliphatic alcohol selected from the group consisting of methanol and ethanol, and/or sorbose, and
   (ii) removing water and the lower aliphatic alcohol and/or the sorbose from the reaction product mixture by membrane pervaporation by bringing the reaction product into contact with an organic membrane having a flux density for methanol of 2.2 to 5 kg/(hm$^2$) under a temperature condition of about 60° C. to about 130° C. and under pressure conditions of a pressure on a retentate side of the membrane of up to 16 bar and a pressure on a permeate side of the membrane of about 1 to 500 mbar to cause traversal of an azeotropic limiting line of the reaction product mixture.

2. A process for recovering acetals or ketals from a reaction product mixture obtained by reacting aldehydes or ketones with alcohols in the presence of a solid acid, wherein the process comprises:
   (i) subjecting the reaction product mixture containing an acetal or ketal together with water and unreacted aldehyde or ketone and alcohol to treatment with a solid base followed by,
   (ii) subjecting the treated reaction mixture according to step (i) to membrane pervaporation by bringing the reaction product into contact with an organic membrane having a flux density for methanol of 2.2 to 5 kg/(hm$^2$) under a temperature condition of about 60° C. to about 130° C. and under pressure conditions of a pressure on a retentate side of the membrane of up to 16 bar and a pressure on a permeate side of the membrane of about 1 to 500 mbar to cause traversal of an azeotropic limiting line of the reaction product mixture to remove water and a lower aliphatic alcohol selected from the group consisting of methanol and ethanol and/or sorbose from the reaction product mixture.

3. The process according to claim 1, wherein step (i) is carried out at a temperature between −100° C. and −40° C.

4. The process as in claim 1, wherein the solid acid is a strongly acidic polymer.

5. The process as in claim 4, wherein the strongly acidic polymer is a polystyrene sulfonic acid.

6. The process as in claim 2, wherein the solid base is a weakly basic ion exchange resin.

7. The process as in claim 1, wherein step (i) is practiced by reacting acetone and methanol in the presence of a solid acid at a temperature of below −40° C. to form 2,2-dimethoxypropane as a reaction product.

8. The process as in claim 1 or 2, which comprises using heat from cooling the reaction mixture for the acetalisation or ketalisation reaction to heat the reaction product mixture in a membrane pervaporation unit which comprises the organic membrane.

9. The process according to claim 1 or 2, wherein the organic membrane has a flux density for methanol of 2.2 to 4.9 kg/(hm$^2$).

10. The process according to claim 1 or 2, wherein step (i) is carried out at a temperature between −80° C. and −50° C.

11. A process for recovering acetals or ketals from a reaction product mixture obtained by reacting aldehydes or ketones with alcohols in the presence of a solid acid, wherein the process comprises:

(i) subjecting the reaction product mixture containing an acetal or ketal together with water and unreacted aldehyde or ketone and alcohol to treatment with a solid base followed by, (ii) subjecting the treated reaction product mixture according to step (i) to membrane pervaporation by bringing the reaction product into contact with a ceramic membrane having a flux density for methanol of 2 to 100 kg/(hm$^2$) under a temperature condition of about 60° C. to about 130° C. and under pressure conditions of a pressure on a retentate side of the membrane of up to 16 bar and a pressure on a permeate side of the membrane of about 1 to 500 mbar to cause traversal of an azeotropic limiting line of the reaction product mixture to remove water and a lower aliphatic alcohol selected from the group consisting of methanol and ethanol and/or sorbose from the reaction product mixture.

12. The process according to claim 11, wherein the ceramic membrane has a flux density for methanol of 3.0 to 73.9 kg/(hm$^2$).

13. The process as in claim 11, wherein the solid base is a weakly basic ion exchange resin.

14. The process as in claim 11, which comprises using heat from cooling the reaction mixture for the acetalisation or ketalisation reaction to heat the reaction product mixture in a membrane pervaporation unit which comprises the ceramic membrane.

\* \* \* \* \*